(12) United States Patent
Sianawati et al.

(10) Patent No.: US 6,506,794 B1
(45) Date of Patent: Jan. 14, 2003

(54) AQUEOUS FUNGICIDE DISPERSION

(75) Inventors: Emerentiana Sianawati, Wilmington, DE (US); John Edward Yates, Manchester (GB)

(73) Assignee: Avecia Inc., Wilmington, DE (US)

( * ) Notice: Subject to any disclaimer, the term of this patent is extended or adjusted under 35 U.S.C. 154(b) by 0 days.

(21) Appl. No.: 09/937,573

(22) PCT Filed: Mar. 16, 2000

(86) PCT No.: PCT/GB00/00979

§ 371 (c)(1),
(2), (4) Date: Sep. 26, 2001

(87) PCT Pub. No.: WO00/57702

PCT Pub. Date: Oct. 5, 2000

(30) Foreign Application Priority Data

Mar. 30, 1999 (GB) .............................. 9907269

(51) Int. Cl.$^7$ .................. A01N 47/10; A61K 31/27
(52) U.S. Cl. .................. 514/476; 514/478; 514/479
(58) Field of Search .................. 514/476, 478, 514/479

(56) References Cited

U.S. PATENT DOCUMENTS 4,997,642 A   3/1991   Curtis et al. .................. 424/78

FOREIGN PATENT DOCUMENTS

| DE | 31 16 653 | 1/1991 |
| WO | WO 93/24008 | 12/1993 |
| WO | WO 99/59709 | 11/1999 |

OTHER PUBLICATIONS

Database WPI, Section Ch, Week 199834 Derwent Publications Ltd., London, GB, AN 1998–393347, XP002141286 & JP 10 158110 A (Mitsui Toatsu Chem Inc), Jun. 16, 1998 abstract.

Database WPI, Section Ch, Week 199850 Derwent Publications Ltd., London, GB;, AN 1998–589603 XP002141287 & JP 10 265309 A (Hokko Chem Ind Co Ltd), Oct. 6, 1998 abstract.

*Primary Examiner*—Alton N. Pryor
(74) *Attorney, Agent, or Firm*—Pillsbury Winthrop LLP

(57) ABSTRACT

An aqueous dispersion comprising a halopropargyl compound (HPC) and a partially hydrolysed polyvinyl alcohol (PHPVA). The aqueous dispersions are useful for inhibiting the growth of micro-organisms on or in a medium, especially an industrial medium such as paint films, metal working fluids, wood, latices and plastic materials.

22 Claims, No Drawings

AQUEOUS FUNGICIDE DISPERSION

This application is the National Phase of International Application PCT/GB00/00979 filed Mar. 16, 2000 which designated the U.S. and that International Application was.

The present invention relates to a stable aqueous dispersion of a halopropynyl compound and to its use in inhibiting the growth of micro organisms such as fungi and algae on or in a medium, especially an industrial medium.

Halopropargyl compounds (hereinafter HPC's) are well-known fungicides and the most widely used is 3-iodo-2-propynyl-N-n-butylcarbamate (herein after IPBC). IPBC is available commercially in both solid form and as a liquid concentrate in organic solvents.

During the last few years there has been an increasing demand for industrial biocide formulations which contain low levels of volatile organic compounds (hereinafter low VOC) and particularly a demand for wholly aqueous formulations. Hitherto, this has been difficult to achieve in the case of HPC's such as IPBC because of their low but significant aqueous solubility. Because of this low solubility in water there is a tendency for small particles to dissolve and to be deposited on larger particles. There is, thus, a tendency for the particle size distribution of the aqueous dispersion to change on storage to fewer particles of larger size. This coarsening of the particle size is referred to as "Ostwald ripening" as discussed, for example, in "Crystallisation" by J. W. Mullin, $3^{rd}$ edition, published by Butterworth/Heinemann, paperback edition 1997, pages 288 to 290. This Ostwald ripening manifests itself in instability of the aqueous dispersion, especially under adverse storage conditions and results in layering and sedimentation of the HPC.

We have examined a number of dispersants of both the non-ionic and anionic type which are designed for distributing particulate solids in an aqueous medium. None of those examined have resulted in stable aqueous dispersions of the HPC. However, we have now found that one class of dispersant which exhibits weak surface-active properties does result in aqueous dispersions of HPC's with surprisingly good storage stability especially under freeze/thaw conditions. These dispersants are partially hydrolysed polyvinyl alcohols (hereinafter PHPVA).

According to a first aspect of the present invention there is provided an aqueous dispersion comprising a HPC and a PHPVA.

Preferably, the HPC is a compound of formula 1

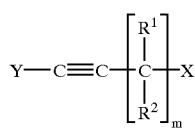

(1)

wherein

Y is halogen;

$R^1$ and $R^2$ are each, independently, $C_{1-6}$-alkyl, $C_{2-6}$-alkenyl or $C_{3-7}$-cycloalkyl;

m is from 1 to 6; and

X is an organic moiety linked to the —$CR^1R^2$— group via an oxygen, nitrogen, sulphur or carbon atom.

Preferably, Y is chlorine, bromine and especially iodine. The compound of formula 1 wherein Y is iodine is an iodopropargyl compound (hereinafter IPC).

The organic moiety linked to the —$CR^1R^2$— group via an oxygen, nitrogen, sulphur or carbon atom preferably contains not greater than 20 and especially not greater than 10 carbon atoms.

The compound of formula 1 wherein the organic moiety is linked to the group —$CR^1R^2$— via an oxygen atom is preferably an ether, ester or especially a carbamate.

The compound of formula 1 wherein the organic moiety is linked to the group —$CR^1R^2$— via a nitrogen atom is preferably an amine or amide.

The compound of formula 1 wherein the organic moiety is linked to the group —$CR^1R^2$— via a sulphur atom is preferably a thiane, sulphone or sulphoxide.

The organic moiety can be alkyl, alkenyl, aryl, heteroaryl, aralkyl, cycloalkyl or cycloalkenyl, all of which may be optionally substituted. When the organic moiety is alkyl, it may be linear or branched but is preferably linear.

Optional substituents in the organic moiety are halogen (preferably chlorine, bromine or iodine), $C_{1-6}$-alkyl and $C_{1-6}$-alkoxy.

Preferably, $R^1$ and $R^2$ are both hydrogen.

Preferably m is one.

According to a first preferred embodiment of the invention the IPC is a compound of formula 2

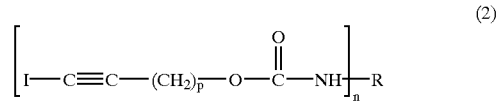

(2)

wherein

R is hydrogen, optionally substituted $C_{1-20}$-alkyl, optionally substituted $C_{2-20}$-alkenyl, optionally substituted aryl, optionally substituted aralkyl, $C_{3-20}$-cycloalkyl or $C_{3-20}$-cycloalkenyl; and n and p are each, independently, from 1 to 3.

When R is $C_{1-20}$-alkyl it is preferably $C_{1-8}$-alkyl or more preferably $C_{1-6}$-alkyl. The alkyl group may be linear or branched. Examples are methyl, ethyl, propyl, sec-butyl, tert-butyl, pentyl, hexyl, heptyl, octyl, nonyl, decyl, dodecyl, octadecyl and especially n-butyl.

When R is aryl, it is preferably phenyl.

When R is aralkyl, it is preferably 2-phenylether or benzyl.

When R is cycloalkyl, it is preferably $C_{4-7}$-cycloalkyl, more preferably cyclopropyl or cyclohexyl.

When R is cycloalkenyl, it is preferably cyclohexenyl.

Preferred optional substituent(s) carried by R include halogen (preferably chlorine, bromine or iodine), $C_{1-6}$-alkyl or $C_{1-6}$-alkoxy. It is preferred, however, that R is unsubstituted.

Preferably n is one. Preferably p is one.

The IPC's of formula 2 are disclosed in U.S. Pat. No. 3,923,870; U.S. Pat. No. 4,259,350; U.S. Pat. No. 4,592,773; U.S. Pat. No. 4,616,004; U.S. Pat. No. 4,719,227 and U.S. Pat. No. 4,945,109.

Especially preferred IPC's of formula 2 are 3-iodo-2-propynyl-N-n-propyl carbamate, 3-iodo-2-propynyl-N-n-butylcarbamate, 3-iodo-2-propynyl-N-n-hexyl carbamate, 3-iodo-2-propynyl-N-cyclohexylcarbamate and 3-iodo-2-propynyl-N-phenyl carbamate.

According to a second aspect of the invention, the IPC is a compound of formula 3

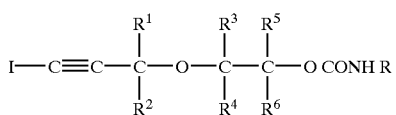
(3)

wherein:

R is defined hereinbefore;

$R^1$ and $R^2$ are each, independently, $C_{1-6}$-alkyl, $C_{2-6}$-alkenyl, $C_{3-7}$-cycloalkyl or —$CR^1R^2$— represents (—$CH_2$)$_t$— where t is from 4 to 6; and $R^3$ to $R^6$ are each, independently, hydrogen, $C_{1-4}$-alkyl, aryl, —$CCl_3$ or $R^3$ with $R^5$ or $R^4$ with $R^6$ represents —($CH_2$)$_q$— where q is from 3 to 5.

The preparation of IPC's of formula 3 are described in, for example U.S. Pat. No. 4,474,807.

Especially, preferred IPC's of formula 3 are 2-(3-iodo-2-propynyloxy)-ethyl-N-methylcarbamate, 2-(3-iodo-2-propynyloxy)-ethyl-N-n-butylcarbamate, 2-(3-iodo-2-propynyloxy)-ethyl-N-phenylcarbamate and 2-(3-iodo-2-propynyloxy)-ethyl-N-(4-chlorophenyl)carbamate.

It is especially preferred that the aqueous dispersion contains an IPC of formula 2 and that the IPC of formula 2 is IPBC.

The PHPVA is preferably obtainable from a polyvinyl ester of an organic acid where the organic acid contains from 1 to 6 carbon atoms excluding the carbonyl carbon atom. Typically the PHPVA is obtainable by partial hydrolysis of the polyvinyl ester of the organic ester, for example by saponification using a suitable base such as KOH or NaOH. Thus, the PHPVA contains both hydroxy groups and $C_{1-6}$-hydrocarbyl-carbonyl radicals. It is preferred that the organic acid is acetic acid whereby the PHPVA is a partially hydrolysed polyvinyl acetate.

Preferably, a 4% aqueous solution of the PHPVA has a viscosity from 2.5 to 42, more preferably from 5 to 27.5 and especially from 7 to 24.5 mPa.s at 20° C. as determined, for example, using DIN 53015.

It is also preferred that the degree of hydrolysis of the partially hydrolysed polyvinyl ester of the organic acid is from 71 to 89 (more preferably from 71.6 to 88.7) mole %.

The ester value of the PHPVA is preferably from 80 to 280 mg KOH/gm, more preferably from 130 to 210 mg KOH/gm and especially from 130 to 150 mg KOH/gm. The ester value refers to the number of mg of KOH required for the neutralisation of the acid released by saponification of 1 g of PHPVA In the case of PHPVA which is derived from polyvinyl acetate, the residual acetyl content is preferably from 7.1 to 22% by weight and especially from 10 to 11.6% by weight.

The amount of HPC in the aqueous dispersion is preferably not less than 1%, more preferably not less than 5% and especially not less than 10% by weight of the total amount of the dispersion. It is also preferred that the amount of HPC is not greater than 60%, more preferably not greater than 50% and especially not greater than 30% by weight based on the total amount of the dispersion.

The amount of PHPVA dispersant in the aqueous formulation depends on the amount of HPC and is preferably from 1 to 10% and especially from 2 to 5% based on the total weight of the dispersion.

The aqueous dispersion may be made by any means known to the art and includes subjecting the HPC to grinding or milling in water in the presence of the PHPVA dispersant to reduce the particle size. Preferably, milling or grinding is continued until the particle size is less than 10µ, more preferably less than 5µ and especially less than 2µ. The particle size of the HPC may be reduced by bead, ball or gravel milling and may be preceded by high-shear mixing in a mixer such as a Silverson mixer.

The aqueous dispersion may contain other adjuvents such as humectants. Preferred humectants have a low vapour pressure at ambient temperatures and therefore a low volatility. Suitable humectants include diols, preferably diols having from 2 to 12 carbon atoms, for example pentane-1,5-diol, ethylene glycol, propylene glycol, butylene glycol, pentylene glycol, hexylene glycol and thiodiglycol and oligo- and poly-alkyleneglycols, preferably diethylene glycol, triethylene glycol, polyethylene glycol (preferably with an average $M_n$<1000, more preferably <500) and polypropylene glycol (preferably with an average $M_n$<1000); triols, preferably glycerol and 1,2,6-hexanetriol; mono-$C_{1-4}$-alkyl ethers of diols, preferably mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)-ethoxy]-ethanol and ethyleneglycol monoallylether; and urea. More preferably the humectant is ethyleneglycol, propyleneglycol, polyethyleneglycol and especially glycerol.

The amount of humectant in the aqueous formulation is preferably from 1 to 10% and especially from 2 to 7% by weight of the total dispersion. We have found that the presence of a humectant reduces the tendency for the HPC particles to aggregate in the aqueous dispersion under freeze/thaw conditions.

The aqueous dispersion may also contain a compound which gives structure to water and which can inhibit the sedimentation of the HPC. Examples of such compounds are polysaccharides, xanthan gum, sodium magnesium silicate, heteropolysaccharides, alginates, carboxymethyl cellulose, gum arabic and polyacrylic acid. Xanthan gum is preferred. Preferably, the amount of such compounds in the dispersion is from 0.1 to 0.5% and especially from 0.3 to 0.4% based on the total weight of the dispersion. Preferably the aqueous dispersion has a viscocity at 20° C. of from 1000 to 4000 cP, more preferably from 1500 to 3500 cP, especially from 1600 to 2500 cP and more especially about 2000 cP as measured at an applied shear rate of 2.3 reciprocal seconds.

Preferably the aqueous dispersion is free from dispersants and/or surfactants other than the PHPVA. We have found that the presence of some additional dispersants and/or surfactants in the aqueous dispersion can cause undesirable crystal growth of the HPC, and therefore an unstable dispersion, during long term storage. It is especially preferred that the aqueous dispersion is free from anionic surfactants/dispersants and non-ionic surfactants/dispersants other than the PHPVA.

Preferably the aqueous dispersion is substantially free from volatile organic compounds. The presence of such compounds is undesirable because there are increasingly stringent environmental regulations requiring formulations to have low VOC content. It is preferred that the aqueous dispersion contains less than 5%, more preferably less than 1% volatile organic compounds.

In an embodiment of the present invention the aqueous dispersion further comprises one or more further antimicrobial compound(s) in addition to the HPC. The presence of further antimicrobial compound(s) can provide a broader spectrum of antimicrobial activity than the HPC alone. Furthermore, the combination of the HPC and further additional antimicrobial compound(s) may provide a synergistic effect.

The further antimicrobial compound or compounds may possess anti-bacterial, anti-fungal, anti-algal or other antimicrobial activity.

Examples of further antimicrobial compounds which may be used, together with the HPC include quaternary ammonium compounds for example, N,N-diethyl-N-dodecyl-N-benzylammonium chloride, N,N-dimethyl-N-octadecyl-N-(dimethylbenzyl)ammonium chloride, N,N-dimethyl-N,N-didecylammonium chloride, N,N-dimethyl-N,N-didodecylammonium chloride; N,N,N-trimethyl-N-tetradecylammonium chloride, N-benzyl-N,N-dimethyl-N-($C_{12}$–$C_{18}$alkyl)ammonium chloride, N-(dichlorobenzyl)-N,-N-dimethyl-N-dodecylammonium chloride, N-hexadecylpyridinium chloride, N-hexadecylpyridinium bromide, N-hexadecyl-N,N,N-trimethylammonium bromide, N-dodecylpyridinium chloride, N-dodecylpyridinium bisulphate, N-benzyl-N-dodecyl-N,N-bis(beta-hydroxy-ethyl)ammonium chloride, N-dodecyl-N-benzyl-N,N-dimethylammonium chloride, N-benzyl-N,N-dimethyl-N-($C_{12}$–$C_{18}$ alkyl)ammonium chloride, N-dodecyl-N,N-dimethyl-N-ethylammonium ethylsulphate, N-dodecyl-N,N-dimethyl-N-(1-naphthylmethyl)ammonium chloride, N-hexadecyl-N,N-dimethyl-N-benzylammonium chloride, N-dodecyl-N,N-dimethyl-N-benzylammonium chloride or 1-(3-chloroallyl)-3,5,7-triaza-1-azoniaadamantane chloride; urea derivatives for example 1,3-bis(hydroxymethyl)-5,5-dimethylhydantoin, bis(hydroxymethyl)urea, 3-(3,4-dichlorophenyl)-1,1-dimethylurea (Diuron), 3-(4-isopropylphenyl)-1,1-dimethylurea, tetrakis(hydroxymethyl)-acetylenediurea, 1-(hydroxymethyl)-5,5-dimethylhydantoin or imidazolidinylurea; amino compounds for example 1,3-bis(2-ethylhexyl)-5-methyl-5-aminohexahydro-pyrimidine, hexamethylenetetramine, 1,3-bis(4-aminophenoxy)propane, dodecylamine or 2-[(hydroxymethyl)-amino]ethanol; imidazole derivatives for example 1[2-(2,4-dichlorophenyl)-2-(2-propenyloxy)ethyl]-1H-imidazole or 2-(methoxycarbonyl-amino)-benzimidazole (Carbendazim); nitrile compounds for example 2-bromo2-bromomethyl-glutaronitrile, 2-chloro-2-chloro-methylglutaro-nitrile, 1,2-dibromo-2,4-dicyanobutane or 2,4,5,6-tetrachloro-1,3-benzenedicarbonitrile (Chlorothaolnil); thiocyanate derivatives for example methylene(bis)thiocyanate or 2-(thiocyanomethylthio)-benzothiazole; tin compounds or complexes for example tributyltinoxide, chloride, naphthoate, benzoate or 2-hydroxybenzoate; isothiazolin-3-ones, for example 4,5-trimethylene4-isothiazolin-3-one, 2-methyl-4,5-trimethylene-4-isothiazolin-3-one, 2-methylisothiazolin-3-one, 5-chloro-2-methyl-isothiazolin-3-one, benzisothiazolin-3-one; 2-methylbenzisothiazolin-3-one, 2-n-butylbenzisothiazolin-3-one, 2-octylisothiazolin-3-one or 4,5-dichloro-2-octylisothiazolin-3-one; thiazole derivatives for example, 2-(thiocyanomethylthio)-benzthiazole or mercaptobenzthiazole; nitro compounds for example, tris(hydroxymethyl)nitromethane, 5-bromo-5-nitro-1,3-dioxane or 2-bromo-2-nitropropane-1,3-diol (Bronopol); iodine compounds, for example tri-iodo allyl alcohol; aldehydes and aldehyde release agents, for example glutaraldehyde (pentanedial), formaldehyde or glyoxal; amides for example chloracetamide, N,N-bis(hydroxymethyl)chloracetamide, N-hydroxymethyl-chloracetamide or dithio-2,2-bis(benzmethylamide); guanidine derivatives for example poly(hexamethylenebiguanide) or 1,6-hexamethylene-bis[5-(4-chlorophenyl)biguanide]; thiones for example 3,5-dimethyltetrahydro-1,3,5-2H-thiodiazine-2-thione; sulphamides, for example N-dimethyl-N'-phenyl-(fluorodichloromethylthio)sulphamide (Preventol A4); triazine derivatives for example hexahydrotriazine, 1,3,5-tri-(hydroxyethyl)-1,3,5-hexahydrotriazine, 6-chloro-2,4-diethyl-amino-s-triazine or 4-cyclopropylamino-2-methylthio-6-t-butylamino-s-triazine (Irgarol); oxazolidine and derivatives thereof for example bis-oxazolidine; furan and derivatives thereof for example 2,5-dihydro-2,5-dialkoxy-2,5-dialkylfuran; antimicrobial carboxylic acids and the salts and esters thereof for example sorbic acid and 4-hydroxybenzoic acid and their salts and esters; phenol and derivatives thereof for example 5-chloro-2-(2,4-dichlorophenoxy)phenol, thio-bis(4-chlorophenol) or 2-phenylphenol; sulphone derivatives for example diiodomethyl-paratolylsulphone, 2,3,5,6-tetrachloro-4-(methylsulphonyl)pyridine or hexachlorodimethylsulphone; imides for example, N-(fluorodichloromethylthio)phthalimide (Preventol A3), N-(trichloromethylthio)phthalimide (Folpet) or N-(trichloromethyl)thio-4-cyclohexene-1,2-dicarboxyimide (Captan); thioamides for example dimethyidithiocarbamate and its metal complexes, ethylenebisdithiocarbamate and its metal complexes, or 2-mercapto-pyridine-N-oxide and its metal complexes and salts (especially the 2:1 zinc complex and the sodium salt); azole fungicides for example hexaconazole, tebuconazole, propiconazole, etaconazole or tetraconazole; strobilurins, for example methyl-(E)-2-[2-(6-(2-cyanophenoxy)pyrimidin-4-yloxy)phenyl]-3-methoxyacrylate (Azoxystrobin), methyl-(E)-methoxyimino[α-(o-tolyloxy)-o-tolyl]acetate, N-methyl-(E)-methoxyimino[2-(2,5-dimethylphenoxymethyl)phenyl]acetamide, N-methyl-(E)-2-methoxyimino-2-(2-phenoxyphenyl)acetamide (Metominostrobin) or Trifloxystrobin.

The amount of further antimicrobial compound(s) in the aqueous dispersion will depend upon the further antimicrobial compound and the medium on or in which the dispersion will be used to protect against microbial degradation. Preferably the weight ratio of the HPC:further antimicrobial compound(s) is from 10:1 to 1:10, more preferably from 5:1 to 1:5 and especially from 2:1 to 1:2.

The further antimicrobial compound(s) may be added to the aqueous dispersion of the HPC and PHPVA directly or in any convenient form, for example as an emulsion, a micro-emulsion or as a solution, preferably an aqueous solution. When the additional antimicrobial compound is a solid which is insoluble in water it is preferably added to the HPC and PHPVA during milling/grinding to form a co-dispersion with the HPC.

Alternatively, the further antimicrobial compound may be added to the aqueous dispersion of the HPC and PHPVA as an aqueous dispersion.

In a preferred embodiment of the invention the aqueous dispersion comprises a HPC; a PHPVA; and 2,4,5,6-tetrachloro-1,3-benzenedicarbonitrile (Chlorothaolnil), wherein the HPC and PHPVA are as hereinbefore defined. We have found that this dispersion is particularly effective for inhibiting the growth of fungi in or on a medium, particularly an industrial medium and especially in paint films.

In view of the foregoing preferences a preferred aqueous dispersion comprises:
(a) from 1 to 60, more preferably from 10 to 50 parts of IPBC;
(b) from 1 to 10, more preferably from 2 to 5 parts of a partially hydrolysed polyvinylacetate, wherein the degree of hydrolysis is from 71.6 to 88.7 mole %; and
(c) from 0 to 40, more preferably 0 to 10 parts in total of one or more further antimicrobial compound(s) other than IPBC (preferably Chlorthalonil);

(d) from 0 to 10, more preferably 1 to 10 parts humectant (preferably glycerol); and
(e) from 30 to 98 parts water;
wherein all parts are by weight and the sum of the parts (a)+(b)+(c)+(d)+(e)=100.

The aqueous dispersion according to the present invention is used to inhibit the growth of micro-organisms such as fungi and algae in or on a medium, preferably an industrial medium. Examples of industrial media include paint films, wood, leather, adhesives, tarpaulins, cellulose canvas, silicone sealants, metal working fluids, polymer emulsions, cooling waters, lacquers, varnishes, masonary, buildings, geological drilling lubricants and plastics materials such as polyurethanes, polyamines, polyesters, polyacrylonitrile, polyolefins and PVC, particularly plasticised PVC.

According to a second aspect of the present invention there is provided a medium treated with an aqueous dispersion according to the first aspect of the present invention. The medium is preferably an industrial medium as hereinbefore defined.

According to a third aspect of the present invention there is provided a method for inhibiting the growth of micro-organisms on or in a medium comprising adding thereto an aqueous dispersion according to the first aspect of the present invention.

The preferred aqueous dispersions are as hereinbefore described in relation to the first aspect of the invention.

The invention is further illustrated by the following examples wherein all references to amounts are in parts by weight unless expressed to the contrary.

EXAMPLE 1

3-lodo-2-propynyl-N-n-butyl carbamate (300 parts, IPBC, ex Mitsui), 10% aqueous solution of partially hydrolysed polyvinyl acetate (300 parts, Mowiol 18–88 ex Hoechst), glycerol (50 parts) and water (350 parts) were pre-milled in a Silverson mixer and then bead-milled in the presence of 1 mm glass beads (3000 parts) in a Blackley mill for about 2 hours until the average particle size of the IPBC was below $2\mu$ as measured using optical microscopy and a Fritsch A22 Analysette Particle Sizer. After removing the glass beads, xanthan gum (40 parts, Keltrol RD ex Kelco) was added and the dispersion mixed under high shear in a Silverson mixer.

No separation or sedimentation of the IPBC dispersion was obtained after 14 freeze/thaw cycles involving 12 hours at −10° C. followed by 12 hours at 40° C. (representing approximately two years simulated storage). The average particle size of the IPBC after the 14 freeze/thaw cycles was less than 5 $\mu$m.

Example 1 illustrates that the aqueous dispersion of the IPBC and partially hydrolysed polyvinyl acetate was stable under adverse storage conditions of freeze-thaw and that Oswald ripening was insignificant.

COMPARATIVE EXAMPLE 1

The aqueous dispersion described in Example 1 was prepared except in place of the partially hydrolysed polyvinyl acetate there was used Agrilan F502 ex Akcros (a non-ionic dispersant).

After just one freeze thaw cycle sedimentation was evident. Examination of the sediment under a microscope revealed large needle-like crystals of IPBC had formed typically with a length in excess of 100 $\mu$m.

The results from Comparative Example 1 illustrate that aqueous dispersions prepared without the partially hydrolysed polyvinyl acetate are not stable and are prone to rapid Ostwald ripening.

EXAMPLES 2 TO 7

The aqueous dispersions shown in Table 1 were prepared using the method described in Example 1. The average particle size of the IPBC was measured and the aqueous dispersion was subjected to 14 freeze/thaw cycles as described in Example 1. Samples of the dispersions were then observed using an optical microscope to assess the degree of crystal growth. The average particle size of the IPBC in the dispersions was also re-measured as described in Example 1.

In Table 1 under the column "Crystal Growth" the following descriptors are referred to:

"OK" A stable dispersion in which the average particle size was <7$\mu$m.

"Slight" Average particle size of from 7 up to 10 $\mu$m.

"Moderate" Average particle size of from 10 to 12 $\mu$m.

"Poor" Unstable dispersion with an average particle >12 $\mu$m.

Under the column marked "Aggregation" the descriptors refer to the aggregates of IPBC crystals observed after the freeze-thaw cycles using an optical microscope. The degree of aggregation was assessed on a scale of "OK" to "Poor" wherein "OK" very few/no aggregates observed; and "Poor" refers to large numbers of aggregates observed.

TABLE 1

| Example | IPBC (%) | PHPVA | PHPVA (%) | Humectant/ additive | Humectant/ additive (%) | Crystal Growth | Aggregation |
|---|---|---|---|---|---|---|---|
| 2 | 30 | M18-88 | 1.8 | — | — | OK | mod |
| 3 | 30 | M18-88 | 2.4 | — | — | OK | slight |
| 4 | 30 | M18-88 | 3 | Glycerol | 2 | slight | OK |
| 5 | 30 | M18-88 | 3 | PEG 400 | 2 | OK | mod |
| 6 | 30 | M18-88 | 3 | Glycerol | 5 | OK | OK |
| 7 | 30 | M18-88 | 3 | PEG 400 | 5 | OK | OK |
| Comparative 2 | 30 | M18-88 | 3 | Agrilan F502 | 0.1 | poor | poor |
| Comparative 3 | 30 | M18-88 | 3 | sod. Dod sulpho | 1.5 | poor | OK |

Footnote to Table 1
M18-88: Mowiol 18-88 a partially hydrolysed polyvinylacetate ex Hoechst
Sod. Dod Sulpho sodium dodecylsulphonate, an anionic surfactant.
Agrilan F502 a non-ionic surfactant ex Akcros.
PEG 400 polyethyleneglycol, average $M_n$ 400.

Comparative Examples 2 and 3 illustrate that the presence of conventional anionic or non-ionic surfactants in the aqueous dispersion according to the present invention can result in undesirable crystal growth.

EXAMPLE 8

The following aqueous dispersion was prepared using the method described in Example 1, except that the IPBC was milled together with the Chlorothalonil:

| | |
|---|---|
| IPBC (ex Troy) | 15 |
| Chlorothalonil (ex GB Bioscience) | 30 |
| Mowiol 18-88 (10% solution in water) | 40 |
| Propylene Glycol | 5 |
| FG-10 | 0.25 |
| Kelzan | 0.20 |
| Water | 9.55 |

FG-10 is a silicon based defoamer ex. Dow Corning.

The resulting aqueous dispersion was found to be stable and no significant Ostwald ripening was observed after storage under freeze/thaw conditions.

What is claimed is:

1. An aqueous dispersion comprising a halopropargyl compound (HPC) and a partially hydrolysed polyvinyl alcohol (PHPVA).

2. An aqueous dispersion as claimed in claim 1 wherein the HPC is a compound of formula 1

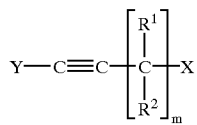

(1)

wherein:
Y is halogen;
$R^1$ and $R^2$ are each, independently, $C_{1-6}$-alkyl, $C_{2-6}$-alkenyl or $C_{3-7}$-cycloalkyl;
m is from 1 to 6; and
X is an organic moiety linked to the group —$CR^1R^2$— via an oxygen, nitrogen, sulphur or carbon atom.

3. An aqueous dispersion according to either claim 1 or claim 2 wherein the HPC is a carbamate.

4. An aqueous dispersion as claimed in claim 1 where the HPC is a compound of formula 2:

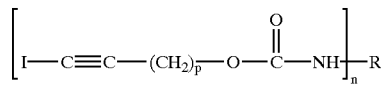

(2)

wherein:
R is hydrogen, optionally substituted $C_{1-20}$-alkyl, optionally substituted $C_{2-20}$-alkenyl, optionally substituted aryl, optionally substituted aralkyl, $C_{3-20}$-cycloalkyl and $C_{3-20}$-cycloalkenyl; and
n and p are each, independently, from 1 to 3.

5. An aqueous dispersion according to claim 1 wherein the HPC is 3-iodo-2-propynyl-N-n-propyl carbamate, 3-iodo-2-propynyl-N-n-butyl carbamate, 3-iodo-2-propynyl-N-n-hexyl carbamate, 3-iodo-2-propynyl-N-cyclohexyl carbamate or 3-iodo-2-propynyl-N-phenyl carbamate.

6. An aqueous dispersion according to claim 1 wherein the HPC is a compound of formula 3

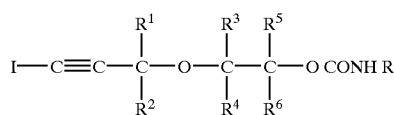

(3)

wherein:
R is hydrogen, optionally substituted $C_{1-20}$-alkyl, optionally substituted $C_{2-20}$-alkenyl, optionally substituted aryl, optionally substituted aralkyl, $C_{3-20}$-cycloalkyl and $C_{3-20}$-cycloalkenyl;
$R^1$ and $R^2$ are each, independently, $C_{1-6}$-alkyl, $C_{2-6}$-alkenyl, $C_{3-7}$-cycloalkyl or —$CR^1R^2$— represents (—$CH_2$)$_t$—where t is from 4 to 6; and
$R^3$ to $R^6$ are each, independently, hydrogen, $C_{1-4}$-alkyl, aryl, —$CCl_3$ or $R^3$ with $R^5$ or $R^4$ with $R^6$ represents —(CH$_2$)$_q$— where q is from 3 to 5.

7. An aqueous dispersion according to claim 6 wherein the HPC is 2-(3-iodo-2-propynyloxy)-ethyl-N-methyl carbamate, 2-(3-iodo-2-propynyloxy)-ethyl-N-n-butyl carbamate, 2-(3-iodo-2-propynyloxy)-ethyl-N-phenyl carbamate or 2-(3-iodo-2-propynyloxy)-ethyl-N-(4-chlorophenyl) carbamate.

8. An aqueous dispersion according to claim 1 wherein the HPC is from 1 to 60% based on the total weight of the dispersion.

9. An aqueous dispersion according to claim 1 wherein the amount of PHPVA is from 1 to 10% based on the total weight of the dispersion.

10. An aqueous dispersion according to claim 1 which further comprises a humectant.

11. An aqueous dispersion according to claim 1 which is free from dispersants and/or surfactants other than the PHPVA.

12. An aqueous dispersion according to claim 1 comprising:
(a) from 1 to 60 parts of IPBC;
(b) from 1 to 10 parts of a partially hydrolysed polyvinylalcohol, wherein the degree of hydrolysis is from 71.6 to 88.7 mole %; and
(c) from 0 to 40 parts in total of one or more further antimicrobial compound(s) other than IPBC;
(d) from 0 to 10 parts humectant; and
(e) from 30 to 98 parts water;
wherein all parts are by weight and the sum of the parts (a)+(b)+(c)+(d)+(e)=100.

13. A medium treated with an aqueous dispersion according to claim 1.

14. A method for inhibiting the growth of microorganisms on or in a medium comprising adding thereto an aqueous dispersion according to claim 1.

15. An aqueous dispersion comprising a halopropargyl compound (HPC and a partially hydrolysed polyvinyl alcohol (PHPVA) wherein the PHPVA is obtainable from a polyvinyl ester of an organic acid and where the organic acid contains from 1 to 3 carbon atoms excluding the carbonyl carbon atom.

16. An aqueous dispersion according to claim 15 wherein the organic acid is acetic acid.

17. A dispersion according to claim 15 wherein a 4% aqueous solution of the PHPVA has a viscosity from 2.5 to 42 mPa.s at 20° C.

18. An aqueous dispersion according to claim 15 wherein the degree of hydrolysis of the polyvinyl ester of the organic acid is from 71 to 89 mole %.

19. An aqueous dispersion according to claim 15 wherein the ester value of the PHPVA is from 80 to 280 mg KOH/gm.

20. An aqueous dispersion as claimed in claim 15 wherein the PHPVA is obtained from polyvinyl acetate and the residual acetyl content is from 7.1 to 22% by weight.

21. An aqueous dispersion which comprises a halopropargyl compound (HPC) and a partially hydrolysed polyvinyl alcohol (PHPVA) and one or more further antimicrobial compound(s) in addition to the HPC.

22. An aqueous dispersion according to claim 21 wherein the further antimicrobial compound is Chlorothalonil.

* * * * *